(12) United States Patent
Gorny

(10) Patent No.: US 6,506,736 B1
(45) Date of Patent: Jan. 14, 2003

(54) METHOD FOR OBTAINING AND USING A COMBINATION OF A PURINE NUCLEOTIDE AND NITROGEN MONOXIDE DONOR FOR TREATING SEXUAL DYSFUNCTION

(76) Inventor: Philippe Gorny, 131 Avenue Malakoff, 75116 Paris (FR)

( * ) Notice: Subject to any disclaimer, the term of this patent is extended or adjusted under 35 U.S.C. 154(b) by 0 days.

(21) Appl. No.: 09/614,694

(22) Filed: Jul. 12, 2000

Related U.S. Application Data

(63) Continuation-in-part of application No. PCT/FR99/02993, filed on Dec. 2, 1999.

(30) Foreign Application Priority Data

Dec. 2, 1998 (FR) .............................................. 98 15237

(51) Int. Cl.[7] .............................................. A61K 31/70
(52) U.S. Cl. .............................. 514/47; 514/2; 514/45; 514/46; 514/48; 514/561; 514/565; 424/195.1
(58) Field of Search ................................ 514/2, 45, 46, 514/47, 48, 561, 565; 424/195.1

(56) References Cited

U.S. PATENT DOCUMENTS

| | | | |
|---|---|---|---|
| 5,594,032 A | * | 1/1997 | Gonzalez-Cadavid et al. |
| 5,824,669 A | * | 10/1998 | Garvey et al. |
| 5,877,216 A | * | 3/1999 | Place et al. |
| 5,910,316 A | * | 6/1999 | Keefer et al. |
| 6,007,824 A | * | 12/1999 | Duckett et al. |
| 6,127,363 A | * | 10/2000 | Doherty, Jr. et al. |

OTHER PUBLICATIONS

Takahashi, et al., "Effects of Adenosine on Canine Penile Erection", Journal of Urology, Oct. 1992, vol. 148: 1323–1325.

Takahashi, et al., "Effects of adenosine triphosphate on canine penile erection", Int. J. Impotence Res. 1992, 4: 27–34.

Mantelli et al., "The Potent Relaxant Effect of Adenosine in Rabbit Corpora Cavernosa is Nitric Oxide Independent and Mediated by $A_2$ Receptors", Journal of Andrology 1995, 16:312–317.

* cited by examiner

Primary Examiner—James O. Wilson
(74) Attorney, Agent, or Firm—Oliff & Berridge, PLC

(57) ABSTRACT

A method for treating a human being having or suspected of having sexual dysfunction or a disorder of physiological and/or anatomical response to sexual stimulation, said dysfunction or disorder involving erectile tissue of genitalia comprising administering the nitrogen monoxide donor arginine and at least on nucleotide selected from the group consisting of AMP or ATP.

24 Claims, No Drawings

METHOD FOR OBTAINING AND USING A COMBINATION OF A PURINE NUCLEOTIDE AND NITROGEN MONOXIDE DONOR FOR TREATING SEXUAL DYSFUNCTION

BACKGROUND OF THE INVENTION

Field of Invention

The invention relates to obtaining a drug intended to prevent or treat sexual dysfunction in men or women. The invention relates in particular to obtaining a drug able to combat disorders of physiological and/or anatomical response to sexual stimulation in human beings. Such a drug contains a purine and a nitric oxide donor in combination.

It is known that, in men, the erection process is as described schematically below. The erectile tissue of the penis, called corpus cavernosum, is a spongy tissue able to fill with blood. In the resting state, the arteries of the penis are controlled by the adrenergic tonus that keeps them in spasm so that no appreciable blood flow fills the corpus cavernosum. Upon an appropriate stimulation, the nervi erigentes inhibit the adrenergic tonus and release certain mediators favoring dilation of the arteries of the penis, causing blood to accumulate in the corpus cavernosum. The latter enlarges, while the increase in its internal pressure causes it to harden. As it enlarges, it crushes the cavernous veins against the envelope of the erectile body, preventing evacuation of the blood it contains, which maintains the rigidity. After ejaculation, adrenaline is once again released locally, the flow of blood into the arteries also decreases, the pressure in the corpus cavernosum drops, and the blood accumulated in the corpus cavernosum can be evacuated by the veins that are no longer compressed, causing loss of rigidity and return to the resting state.

In women, sexual arousal results in particular in vasodilation of the blood vessels irrigating the genital organs. This vasodilation brings about in particular swelling and erectile response of the clitoris, and congestion of the vaginal wall vessels with exudation of vaginal fluids.

It is known that a fairly high proportion of men (between 10 and 50% depending on the population studied and the age group) suffers from permanent or temporary erectile dysfunction. These difficulties may be organic, in which case they require specific treatments adapted to each cause. However, the majority of erectile dysfunctions are not organic, and are often of psychological origin.

In women as well, the physiological response to sexual arousal and its anatomical manifestations may be temporarily altered, sometimes permanently, even with no detectable organic cause. The difficulties most frequently observed include the absence of sexual desire even after stimulation, difficulty in achieving orgasm, low intensity of sexual pleasure, and decreased or even absent natural vaginal lubrication. They often lead to a lack of interest in sexual activity. These disorders of physiological and/or anatomical response to sexual stimulation are termed "female sexual dysfunction" in the present patent application. According to some estimates, the frequency of temporary or chronic sexual dysfunction in women is equivalent to that of erectile dysfunction in men.

Hence it is desirable to have treatments enabling the severity and/or duration of these disorders to be reduced, or prevent their appearance, and to restore the ability to achieve satisfactory sexual intercourse in subjects, men or women, who have such disorders or fear that they will occur.

For cases of male impotence, various treatments have been proposed. In severe forms, intracavernous injection of vasoactive substances may give good results. In the case of moderate or incipient erectile dysfunction, oral treatments are more appropriate and are generally better accepted. A number of products, often of plant origin, have been proposed for this purpose. The use of an oral vasodilator (WO 96/33705; WO 96/16644) and a transdermal, transmucosal, intranasal, or rectal vasodilator (WO 95/05172) has also been proposed.

Of the known vasodilators, a distinction is made between those with antagonist effects on α-adrenergic receptors (phentolamine for example) which inhibit adrenergic tonus thus favoring dilation of the arteries, and those that play the role of nitric oxide (NO) donors, either directly or during their metabolism. It is known that the endothelial cells that coat the interior of blood vessels are able to secrete a substance that dilates the arteries, this substance being nitric oxide. It has been established that nitric oxide stimulates synthesis of cyclic guanosine monophosphate (or cGMP) which brings about relaxation of the muscles of the arteries. It is also known that nitric oxide is the main physiological neurotransmitter brought into play by the nonadrenergic and noncholinergic peripheral neurons innervating the corpus cavernosum and its arteries, and that its release at the effector synapse is an important factor in inducing erection; see in particular Burnett et al., Science 257:401–403(1992) and Fajfer et al., New Eng. J Med. 326:90–94(1992). International application WO 92/21346 recommends administration of a nitric oxide donor, linsidomine, for treating erectile dysfunction.

Substances acting on dilation of the arteries by producing nitric oxide that may be cited as examples are arginine, sodium nitroprussiate, organic nitrates (glycerol trinitrate, isosorbide mononitrate or dinitrate), organic nitrites (amyl or butyl nitrites), thionitrites as described in document WO 96/16645(e.g. S-nitrosocysteine, S-nitrosoglutathion), molsidomine, and, where applicable, pharmaceutically acceptable salts of these compounds.

It is known that other agents are involved in the physiological phenomenon of turgidity of erectile bodies. Examples of these agents are prostaglandins, vasoactive peptides such as bradykinin, the neuropeptide known as vasoactive intestinal peptide (or VIP), neuropeptide Y, etc. Also, rabbit studies have shown that purines are able to induce relaxation of the corpus cavernosum; see Wu H—Y et al., Int. J. Impotence Res . 5, 161–167(1993). It has also been shown that intravenous injection of adenosine triphosphate induces erection in dogs; see Takahashi Y. et al., Int. J. Impotence Res . 4, 27–34(1992). Purines are reported to act as nonadrenergic noncholinergic neurotransmitters.

It has now been discovered that the combination of purine activity and nitric oxide donor activity gives favorable results in prevention and treatment of disorders of physiological and anatomical response to sexual stimulation in humans (men or women) allowing said disorders to be combatted by a synergistic effect.

In the present application, "nitric oxide donor" is understood to be any agent able to produce in vivo, directly or indirectly, nitric oxide (NO) or any metabolic precursor of such an agent, as well as any agent able to favor production of endogenous nitric oxide, for example phosphodiesterase inhibitors that have the indirect effect of increasing the level of nitric oxide. Nitric oxide donors are in particular the substances referred to hereinabove. Nitric oxide donor activity is obtained by the presence of such an agent.

In the present application, "purine" is understood to be purine bases, particularly adenine, purine-based nucleosides, particularly adenosine, as well as the corresponding phosphates, particularly AMP, ADP, and ATP, as well as their pharmaceutically acceptable salts (for example adenine or adenosine hydrochloride, or adenosine-phosphate sodium salts). More generally, "purine" is understood to be any substance able to act on the purine receptors. Such substances are known or can be detected by known methods. Purine activity is activity obtained by the presence of a purine as defined above.

If a compound has both purine activity and nitric oxide donor activity, it can be used as a single active ingredient in the drug obtained according to the invention.

To study the effects of agents intended to treat disorders of physiological and anatomical response to sexual stimulation in men and women, known methods such as the tests described by Boolell M. et al, Int. J. of Impotence Res ., 8, 47–52 (1996) and PCT WO 95/05172, or the tests described hereinbelow, may be used.

The drug obtained according to the invention is used so that effective doses, that can be determined by simple routine experiments, for example the tests just referred to, are administered to the treated individual. It should be noted that several active purines and many nitric oxide donors are known, as are their active doses. It is also easy to determine the effective doses with the aid of such tests. When the effects of the combination are compared with the effects of each of its active ingredients, it is found that in general the combination enables the doses of at least one of the active ingredients to be reduced. Combinations with a synergistic effect can thus be selected.

Hence, the object of the invention is to use a combination of a purine and a nitric oxide donor agent, with the exception of the use, in combination, of adenosine and linsidomine, as active ingredients in the preparation of a drug intended to prevent or treat disorders of physiological and/or anatomical response to sexual stimulation, and in particular to prevent or treat nonorganic erectile dysfunction. This drug is administered to subjects who need it, i.e. persons who have experienced such disorders or fear that they will occur.

The active ingredients of a drug obtained according to the invention can be supplied separately, each in an appropriate pharmaceutical form, and provided in one package.

However, to facilitate simultaneous administration of the active ingredients, it is generally preferable to prepare the drug in a single pharmaceutical form containing the two active ingredients, or the single active ingredient in the case where the latter has both types of activity (purine activity and nitric oxide donor activity), possibly with the addition of an appropriate pharmaceutical excipient.

The drug obtained according to the invention can be administered by the oral, sublingual, nasal, pulmonary, vaginal, rectal, or transdermal route, or by intracavemous injection.

For this purpose, it may be provided in any form enabling oral administration (in particular in the form of gel capsules, drinkable solutions or emulsions, powders, gels, granulates, lozenges, or tablets), nasally (for example solutions administered in the form of drops or sprays), by the pulmonary route (solutions in pressurized aerosol dispensers), rectally (suppositories), cutaneously (for example ointments or transdermal devices also known as patches), or transmucosally, for example sublingually (solutions in pressurized dispensers, or tablets that crumble in the mouth) or vaginally (particularly vaginal creams or suppositories), or by the intracavemous route (injectable suspensions or solutions).

These pharmaceutical forms are prepared in the usual manner and can contain appropriate classical excipients and vehicles.

The drugs obtained according to the invention are in particular those containing no adenosine, and those containing no linsidomine.

The following may be cited of the combinations used according to the invention: adenosine monophosphate (AMP), or adenosine triphosphate (ATP), with arginine.

L-arginine is a precursor of endogenous nitric oxide, and its administration relaxes the muscles of the arteries and corpus cavemosum, this relaxation being necessary for an erection to be achieved. Administration of 2800mg L-arginine per day is reported to have a favorable effect on erectile dysfunction in approximately 40% of cases; see A. W. Zorgniotti and E. F. Lizza, Int. J. Impotence Res., 6, 33-36(1994).

Arginine can be used in the non-salt or salt form (particularly as the hydrochloride, glutamate, aspartate, or citrate).

The drug according to the invention gives favorable results in men suffering from temporary erectile dysfunction, and also in subjects with chronic erectile dysfunction. In women, improvements are found in particular with at least one of the following disorders: loss or decline of sexual desire, absence of orgasm or difficulty in achieving orgasm, vaginal dryness, reduction in intensity of sexual pleasure, etc.

The drug obtained according to the invention can be used either over long periods in the case of chronic erectile dysfunction (for example treatments lasting several weeks, several times a year) or in episodic treatments for temporary and/or recent erectile dysfunction, or as a one-time treatment.

Such a drug can for example be prepared in a pharmaceutical form allowing administration of 30 to 150 mg of AMP in one or two doses, and also allowing administration of a sufficient dose of arginine, for example one dose of 1 to 8 g per day, usually 1.5 to 3 g, in one or two doses, said dose being calculated by weight of arginine in the freebase form.

For example, a dose of 50 to 100 mg of AMP and 1 to 2 g per day of L-arginine may be administered to adults for a course of treatment lasting 2 to 4 weeks. As a one-time treatment, 60 to 120 mg AMP and 1.5 to 4 g L-arginine in the oral or sublingual form for example can be administered in a single dose approximately 30 minutes to 2 hours before the planned sexual encounter.

AMP can be replaced in particular by equivalent quantities of ATP.

The invention also relates to a method of preventing or treating male or female sexual dysfunction in which a drug as defined above is administered.

Tests have been performed on female volunteers aged 30 to 55, suffering from at least one of the following disorders: loss of sexual desire, inability to achieve orgasm, decreased intensity of sexual pleasure, or vaginal dryness. Packets containing 3 g arginine glutamate and 60 mg AMP in the powder form for suspension in water were given to the test subjects, with the request that they take one packet of powder once a day for two weeks.

The test subjects noted the effects observed by self-evaluating sexual desire, achievement of orgasm, intensity of sexual pleasure, and vaginal lubrication. The majority of test subjects found improvements in at least two of the criteria used for this study.

Similar tests were performed on men aged 38 to 70 suffering from incipient sexual dysfunction. They were asked to take the contents of one packet of powder per day for 10 days and also to ingest the contents of an additional package 30 minutes to two hours before planned sexual activity. Approximately 60% of the individuals tested found that quality or frequency of erection improved.

The invention also relates to a nontherapeutic method for increasing sexual desire and/or sexual capacity and/or favoring sexual activity and/or improving the intensity of sexual pleasure and/or favoring accomplishment of satisfactory sexual encounters, in individuals who wish the above even though they do not suffer from the sexual dysfunctions defined above. This method includes the fact of administering to such individuals a purine and a nitric acid donor, for example between two hours and half an hour before a planned sexual activity. The doses administered can be chosen from the dose ranges indicated hereinabove.

The following example illustrates the invention.

EXAMPLE

Powder Packets for Drinkable Suspensions

Powder packets with the following contents are prepared:

| | |
|---|---|
| AMP: | 60 mg |
| Arginine glutamate: | 3 g |
| Aroma excipient: | 0.5 g |

The AMP can be replaced by an equivalent quantity of ATP.

It is advisable to ingest the contents of one packet every day after suspending it in water. The contents of an additional packet can also be ingested 30 minutes to 2 hours before planned sexual activity.

What is claimed is:

1. A method of treating a human being having or suspected of having sexual dysfunction or a disorder of physiological and/or anatomical response to sexual stimulation, said dysfunction or disorder involving erectile tissue of genitalia, comprising:
   administering to a human being having or suspected of having a sexual dysfunction or a disorder of physiological and/or anatomical response to sexual stimulation arginine and at least one member selected from the group consisting of AMP and ATP.

2. The method of claim 1, wherein said arginine and said at least one member selected from the group consisting of AMP and ATP are administered in the form of a capsule, gel capsule, drinkable solution or emulsion, granule, gel, cream, powder, lozenge, tablet, ointment, transdermal device, vaginal suppository, suppository, or solution.

3. The method of claim 2, wherein said arginine and said at least one member selected from the group consisting of AMP and ATP are administered by injection, by intranasal administration or by pulmonary administration.

4. The method of claim 1, wherein said arginine and said at least one member selected from the group consisting of AMP and ATP are administered in a single pharmaceutical form containing said purine and said nitric oxide donor agent.

5. The method of claim 1, wherein said arginine and said at least one member selected from the group consisting of AMP and ATP are administered in separate pharmaceutical forms, each pharmaceutical form containing one of said arginine and said at least one member selected from the group consisting of AMP and ATP.

6. The method of claim 1, wherein said at least one member selected from the group consisting of AMP and ATP is present in an amount of 30 to 150 mg per one or two doses.

7. The method of claim 1, wherein said arginine is present in an amount of 1 to 8 g per one or two doses, calculated as the weight of arginine in free base form.

8. The method of claim 1, wherein said arginine is present in an amount of 1.5 to 3 g per one or two doses, calculated as the weight of arginine in free base form.

9. The method of claim 1, wherein said at least one member selected from the group consisting of AMP and ATP is AMP and said AMP is present in an amount of 30 to 150 mg per one or two doses.

10. The method of claim 1, wherein said at least one member selected from the group consisting of AMP and ATP is AMP and said AMP is present in an amount of 50 to 100 mg per one or two doses.

11. The method of claim 1, wherein said human being is a man.

12. The method of claim 1, wherein said human being is a woman.

13. A method of at least one of enhancing sexual desire, enhancing sexual pleasure, increasing sexual capacity and increasing sexual stimulation in human beings, comprising:
    administering to a human being not suffering from a sexual dysfunction arginine and at least one member selected from the group consisting of AMP and ATP, wherein said human being desires to enhance his or her sexual desire and/or sexual pleasure by administration of said arginine and said at least one member selected from the group consisting of AMP and ATP.

14. The method of claim 13, wherein said arginine and said at least one member selected from the group consisting of AMP and ATP are in the form of a capsule, gel capsule, drinkable solution or emulsion, granule, gel, cream, powder, lozenge, tablet, ointment, transdermal device, vaginal suppository, suppository, or solution.

15. The method of claim 14, wherein said arginine and said at least one member selected from the group consisting of AMP and ATP are administered by injection, by intranasal administration or by pulmonary administration.

16. The method of claim 13, wherein said arginine and said at least one member selected from the group consisting of AMP and ATP are administered in a single composition.

17. The method of claim 13, wherein arginine and said at least one member selected from the group consisting of AMP and ATP are administered in separate compositions, each composition containing one of said arginine and said at least one member selected from the group consisting of AMP and ATP.

18. The method of claim 13, wherein said at least one member selected from the group consisting of AMP and ATP is present in an amount of 30 to 150 mg per one or two doses.

19. The method of claim 13, wherein said arginine is present in an amount of 1 to 8 g per one or two doses, calculated as the weight of arginine in free base form.

20. The method of claim 13, wherein said arginine is present in an amount of 1.5 to 3 g per one or two doses, calculated as the weight of arginine in free base form.

21. The method of claim 13, wherein said at least one member selected from the group consisting of AMP and ATP is AMP and said AMP is present in an amount of 30 to 150 mg per one or two doses.

22. The method of claim 13, wherein said at least one member selected from the group consisting of AMP and ATP is AMP and said AMP is present in an amount of 50 to 100 mg per one or two doses.

23. The method of claim 13, wherein said human being is a man.

24. The method of claim 13, wherein said human being is a woman.

* * * * *